(12) United States Patent
Ventimiglia et al.

(10) Patent No.: US 11,776,332 B2
(45) Date of Patent: Oct. 3, 2023

(54) IN-VEHICLE SENSING MODULE FOR MONITORING A VEHICLE

(71) Applicant: Robert Bosch GmbH, Stuttgart (DE)

(72) Inventors: Philip Ventimiglia, Northville, MI (US); Krisztian Bakos, Redondo Beach, CA (US); Karl Holodnick, Northville, MI (US); Russell Watts, Ann Arbor, MI (US); George Lewis, Brighton, MI (US); Stefan Weissert, Royal Oak, MI (US)

(73) Assignee: Robert Bosch GmbH, Stuttgart (DE)

(*) Notice: Subject to any disclaimer, the term of this patent is extended or adjusted under 35 U.S.C. 154(b) by 287 days.

(21) Appl. No.: 17/116,165

(22) Filed: Dec. 9, 2020

(65) Prior Publication Data
US 2021/0190516 A1    Jun. 24, 2021

Related U.S. Application Data

(60) Provisional application No. 62/952,623, filed on Dec. 23, 2019, provisional application No. 62/952,618, (Continued)

(51) Int. Cl.
*B60R 11/04* (2006.01)
*G07C 5/08* (2006.01)
(Continued)

(52) U.S. Cl.
CPC ......... *G07C 5/085* (2013.01); *G01C 21/3438* (2013.01); *G01C 21/3484* (2013.01); *G01N 33/0031* (2013.01); *G01N 33/0047* (2013.01); *G01P 15/14* (2013.01); *G01S 19/13* (2013.01); *G01V 8/10* (2013.01); *G06V 20/59* (2022.01); *G07C 5/008* (2013.01); *G07C 5/02* (2013.01);
(Continued)

(58) Field of Classification Search
None
See application file for complete search history.

(56) References Cited

U.S. PATENT DOCUMENTS 7,363,148 B1    4/2008   Laverick et al.
7,889,086 B2    2/2011   Schafer et al.
(Continued)

FOREIGN PATENT DOCUMENTS

CA    2860461 A1 *   7/2013   ............. G01C 21/00
CA    3008512 A1 * 12/2018   ......... G06Q 10/0833
(Continued)

*Primary Examiner* — Jamel E Williams
(74) *Attorney, Agent, or Firm* — Maginot, Moore & Beck LLP

(57) ABSTRACT

A sensing module for monitoring a cabin of a vehicle includes an environmental sensor configured to sense organic compounds in ambient air of the cabin and a particle sensor configured to detect particulate matter in the ambient air. The sensing module further includes a controller operably connected to the environmental sensor and the particle sensor and configured to receive sensor signals from the environmental sensor and the particle sensor and to transmit data to a remote server via the Internet. The sensing module has a housing configured to mount to a windshield of the vehicle. The housing supports the environmental sensor, the particle sensor, and the controller.

18 Claims, 13 Drawing Sheets

Related U.S. Application Data filed on Dec. 23, 2019, provisional application No. 62/952,568, filed on Dec. 23, 2019.

(51) Int. Cl.

| | | |
|---|---|---|
| *G07C 5/02* | (2006.01) | |
| *G01S 19/13* | (2010.01) | |
| *G07C 5/00* | (2006.01) | |
| *G01N 33/00* | (2006.01) | |
| *G01P 15/14* | (2013.01) | |
| *G01V 8/10* | (2006.01) | |
| *H04L 12/18* | (2006.01) | |
| *H04L 67/1097* | (2022.01) | |
| *G01C 21/34* | (2006.01) | |
| *G06V 20/59* | (2022.01) | |
| *B60R 11/00* | (2006.01) | |

(52) U.S. Cl.
CPC ...... *H04L 12/1895* (2013.01); *H04L 67/1097* (2013.01); *B60R 11/04* (2013.01); *B60R 2011/0003* (2013.01); *B60R 2011/0026* (2013.01)

(56) References Cited

U.S. PATENT DOCUMENTS

| | | |
|---|---|---|
| 8,954,204 B2 | 2/2015 | Everhart et al. |
| 9,596,387 B2 | 3/2017 | Achenbach et al. |
| 9,602,779 B2 | 3/2017 | DeJuliis |
| 9,688,194 B2 | 6/2017 | MacNeille et al. |
| 10,196,070 B2 | 2/2019 | Song |
| 10,207,716 B2 | 2/2019 | Liu |
| 10,223,844 B1 | 3/2019 | Schwie |
| 10,252,688 B2 | 4/2019 | Szawarski et al. |
| 10,286,751 B2 | 5/2019 | Jackson |
| 10,445,950 B1 | 10/2019 | De et al. |
| 2015/0371456 A1 | 12/2015 | Moore, Jr. et al. |
| 2019/0197325 A1 | 6/2019 | Reiley et al. |
| 2019/0263217 A1* | 8/2019 | Salter ................ B60H 1/245 |

FOREIGN PATENT DOCUMENTS

| | | | |
|---|---|---|---|
| CN | 1815398 A | * 8/2006 | |
| CN | 104972870 A | * 10/2015 | ............. B60H 1/22 |
| CN | 107199845 B | * 7/2018 | ......... B60H 1/00735 |
| WO | WO-2018049527 A1 | * 3/2018 | |

\* cited by examiner

IN-VEHICLE SENSING MODULE FOR MONITORING A VEHICLE

CROSS-REFERENCE TO RELATED APPLICATIONS

This application claims priority to U.S. Provisional Patent Application Ser. No. 62/952,618, which is entitled "In-Vehicle Sensing Module for Monitoring a Vehicle" and was filed Dec. 23, 2019, to U.S. Provisional Patent Application Ser. No. 62/952,568, which is entitled "In-Vehicle Sensing Module for Monitoring a Vehicle" and was filed Dec. 23, 2019, and to U.S. Provisional Patent Application Ser. No. 62/952,623, which is entitled "In-Vehicle Sensing Module Having Cloud Connectivity" and was filed Dec. 23, 2019, the disclosures of which are incorporated herein by reference in their entirety.

This application is related to U.S. patent application Ser. No. 17/116,133, filed on filed on even date herewith, and to U.S. patent application Ser. No. 17/116,142, filed on even date herewith, the disclosures of which are incorporated herein by reference in their entirety.

FIELD

The device and method disclosed in this document relates to in-vehicle sensing and, more particularly, to an in-vehicle sensing module.

BACKGROUND

Unless otherwise indicated herein, the materials described in this section are not prior art to the claims in this application and are not admitted to the prior art by inclusion in this section.

In shared vehicle services, such as ride sharing services, taxi services, and car rental services, shared vehicles are often driven by drivers or ridden in by passengers who are not the owner of the vehicle. A common problem with such services is that customers can be careless about how they treat the vehicle during their short time as a passenger or driver. In light of this, operators of such services often put in place various rules or policies regarding how the vehicle should be treated by the customer. However, modern incarnations of these services are technology driven and often entirely autonomous, so as to require little or no direct interaction with the owner of the vehicle or the operator of the service. As a result, effective enforcement of these rules or policies can be challenging and sometimes cost-prohibitive. Accordingly, it would be beneficial to provide a system that enables autonomous detection of issues within the vehicle that minimizes the need for human intervention in enforcing rules or policies, as well as remedying violations.

SUMMARY

In one embodiment, a sensing module for monitoring a cabin of a vehicle includes an environmental sensor configured to sense organic compounds in ambient air of the cabin and a particle sensor configured to detect particulate matter in the ambient air. The sensing module further includes a controller operably connected to the environmental sensor and the particle sensor and configured to receive sensor signals from the environmental sensor and the particle sensor and to transmit data to a remote server via the Internet. The sensing module has a housing configured to mount to a windshield of the vehicle. The housing supports the environmental sensor, the particle sensor, and the controller.

In another embodiment, a sensing module for monitoring a cabin of a vehicle includes an environmental sensor configured to sense organic compounds in ambient air of the cabin, a particle sensor configured to detect particulate matter in the ambient air, the particle sensor including an inlet, and a controller operably connected to the environmental sensor and the particle sensor and configured to receive sensor signals from the environmental sensor and the particle sensor and to transmit data to a remote server via the Internet. The sensing module further includes a housing configured to mount to a windshield of said vehicle. The housing defining an interior space in which the environmental sensor, the particle sensor, and the controller are supported, and the interior space has an inlet region from which the inlet of the particle sensor draws air. The inlet region is substantially isolated from a remainder of the interior space and has a volume that is less than 10% of an overall volume of the interior space.

In yet another embodiment, a sensing module for monitoring a cabin of a vehicle includes an environmental sensor configured to sense organic compounds in ambient air of the cabin, a particle sensor configured to detect particulate matter in the ambient air, and a controller operably connected to the environmental sensor and the particle sensor and configured to receive sensor signals from the environmental sensor and the particle sensor and to transmit data to a remote server via the Internet. A printed circuit board ("PCB") is supported in the housing and operably connects the controller, the environmental sensor, and the particle sensor to one another. The controller and the environmental sensor are arranged on the PCB. In addition, the module includes at least one microphone arranged on the PCB, and a housing configured to mount to a windshield of said vehicle. The housing supports the environmental sensor, the particle sensor, the controller, and the PCB, and includes at least one opening assigned to each microphone.

BRIEF DESCRIPTION OF THE DRAWINGS

The foregoing aspects and other features of an in-vehicle sensing system are explained in the following description, taken in connection with the accompanying drawings.

DETAILED DESCRIPTION

Figure 1:
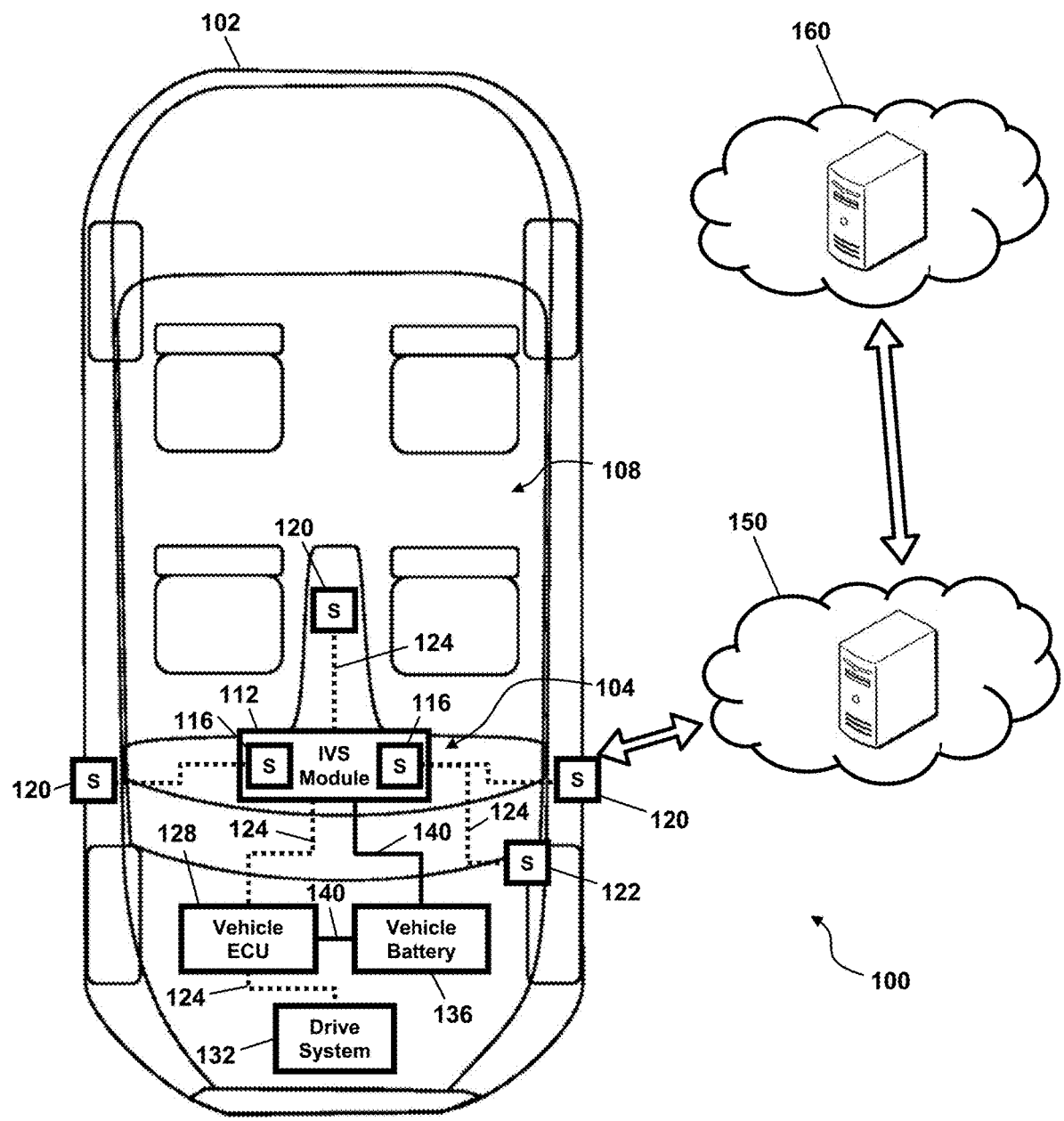
FIG. 1 shows a simplified block diagram of a vehicle having an in-vehicle sensing system that includes an in-vehicle sensing module for monitoring the vehicle.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

System Overview

FIG. 1 shows a simplified block diagram of a vehicle monitoring system 100 having an in-vehicle sensing system 104 for monitoring at least a cabin 108 of a vehicle 102. The vehicle monitoring system 100 is advantageous for use in the context of a shared vehicle service in which the shared vehicle 102 is driven by drivers or ridden in by passengers who are not the owner of the shared vehicle 102. Such shared vehicle services might include, but are not limited to, a car rental service, an autonomous taxi service, or a ride sharing service. In many such shared vehicle services, a customer may engage the services of the shared vehicle service in an automated manner using a smartphone application, a website, an on-site kiosk, or the like, which involves little or no direct human intervention by the operator of the shared vehicle service.

The in-vehicle sensing system 104 advantageously enables operators of shared vehicle to monitor the condition of the vehicle 102, enforce rules and policies, and provide additional benefits to the customer with minimal human intervention. Such rules and policies might include rules against smoking the vehicle 102 or surcharges for any required cleaning of the vehicle 102 after usage by the customer. Additionally, the operator can provide additional benefits to the customer, such as notifying the customer of personal property left in the vehicle after the conclusion of a ride.

The in-vehicle sensing system 104 includes an in-vehicle sensing module 112 having one or more integrated sensors 116 configured to monitor a status of at least the cabin 108. In some embodiments, an in-vehicle sensing system 100 further includes additional external sensors 120 and a gyroscope/accelerometer module 122 arranged on or throughout the vehicle 102, which are operably connected to the in-vehicle sensing module 108 via one or more communication buses 124. In one embodiment, the in-vehicle sensing module 112 and at least the integrated sensors 116 are integrated in a chassis and/or enclosure, which is adapted for retrofitting into a particular make and model of the vehicle 102. The sensors 116, 120 and algorithms (discussed below) used by the in-vehicle sensing module 112 may also be specific to particular make and model of the vehicle 102. Alternatively, in some embodiments, the in-vehicle sensing system 104 is usable in any desired vehicle, and the housing of the in-vehicle sensing module 112 is configured to be mounted on a surface within the cabin 108 of the shared vehicle 102, such as, for example, a dash or windshield.

In addition to the in-vehicle sensing system 104, the vehicle 102 includes a vehicle electronic controller ("ECU") 128, a drive system 132, and a vehicle battery 136. In one embodiment, the vehicle ECU 128 is configured to operate the drive system 132, as well as various electronics of the vehicle, such as lights, locks, speakers, displays, etc. The vehicle ECU 128 may communicate with these various electronics and the drive system 132, as well with as the in-vehicle sensing system 104, via the one or more communication buses 124. In one embodiment, the vehicle ECU 128 communicates certain telemetric data to the in-vehicle sensing module 112, such as vehicle speed or travel direction and, thus, the vehicle ECU 128 may be considered one of the external sensors 120.

The drive system 132 of the vehicle 102 includes a drive motor, for example an internal combustion engine and/or one or more electric motors, that drives the wheels of the vehicle 102, and the steering and braking components that enable the vehicle 102 to be moved in a controlled manner. The vehicle battery 136 is configured to provide operating power (e.g., via a 12V accessory power line 140, or the like) to the in-vehicle sensing module 112, the external sensors 120, the gyroscope/accelerometer module 122, the vehicle ECU 128, and/or any other vehicle electronics of the vehicle 102.

The in-vehicle sensing module 112 includes at least a processor, a memory, and the one or more integrated sensors 116 integrated into a common enclosure that is installed into the cabin 108 of the vehicle. The in-vehicle sensing module 112 is configured to monitor a status of at least the cabin 108 of the vehicle. Particularly, the in-vehicle sensing module 112 is configured to process sensor data received from the sensors 116, 120 to infer one or more qualities, conditions, or statuses of the vehicle 102. For example, the in-vehicle sensing module 112 may detect whether the vehicle 102 is empty, whether the vehicle 102 is clean, whether the vehicle 102 has been damaged, whether the vehicle 102 has been subjected to cigarette smoke or other unpleasant smells, and/or whether an object has been left behind in the vehicle 102. The in-vehicle sensing module 112 utilizes appropriate algorithms, models (e.g., artificial neural networks), or thresholds to interpret the sensor data and enrich the data with metadata and event detection. It will be appreciated by those of ordinary skill in the art that the term "metadata" refers to any data that describes or gives information about other data (e.g., the sensor data).

To this end, depending on the particular qualities, conditions, or statuses of the vehicle 102 to be monitored, the sensors 116, 120 may comprise a wide variety of sensors including, for example, cameras, microphones, gyroscopes, accelerometers, smoke detectors or other air-quality/particle sensors, temperature sensors, and/or humidity sensors. The gyroscope/accelerometer module 122 may include, for example, a microphone, a gyroscope, and an accelerometer integrated in a single housing that is affixed to the chassis of the vehicle.

The in-vehicle sensing module 112 is configured to upload, by a cellular Internet connection, relevant sensor data, event data, or other metadata to a cloud storage backend 150 for storage thereat. The data uploaded to the cloud storage backend 150 is accessible by a third-party cloud backend 160. The third-party backend 160 is, for example, associated with the shared vehicle service discussed above, such as a car rental service, an autonomous taxi service, or a ride sharing service. In this way, an operator of the shared vehicle service can monitor the condition of the shared vehicle 102, enforce rules and policies, and provide additional benefits to the customer with minimal human intervention.

In-Vehicle Sensing Module with Integrated Camera

Figure 2:
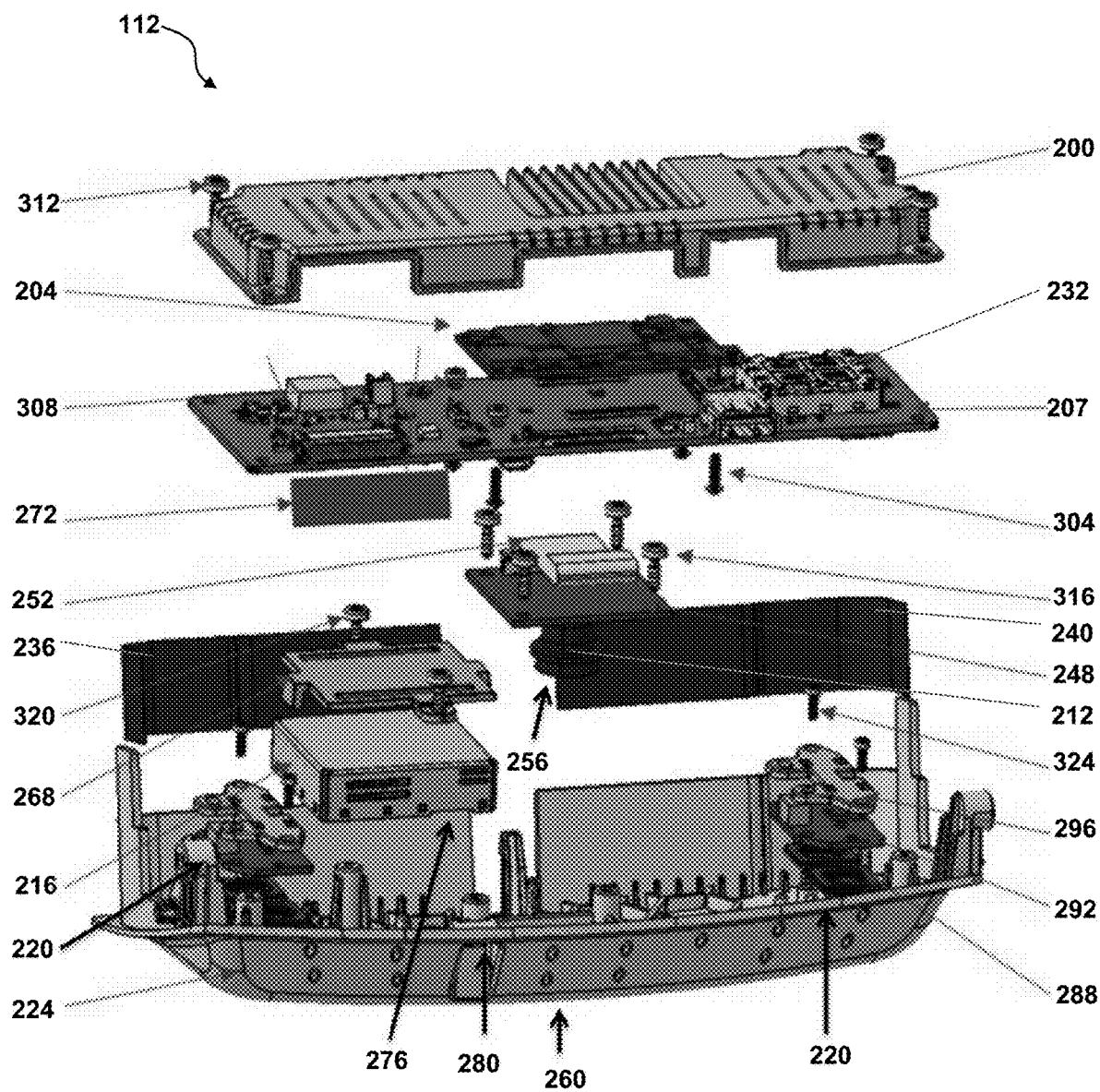
FIG. 2 shows an exploded view of the in-vehicle sensing module of FIG. 1.

FIG. 2 depicts an exploded view of one embodiment of the in-vehicle sensing module 112 configured for mounting in the overhead console of a vehicle. The in-vehicle sensing module 112 includes a heatsink 200, a system on a module (SoM) 204, a module printed circuit board (PCB) 208, a camera 212, a particle sensor 216, a plurality of LED arrangements 220, and a lower housing 224.

The heatsink 200 is formed of thermally-conductive material, for example an aluminum alloy, and includes vents configured to allow air to flow away from the electronic components. Additionally, the heatsink 200 includes a plurality of fins that dissipate heat from the electronic components. The heatsink 200 defines a plurality of apertures or notches in the sides of the heatsink 200 that allow access to connection terminals of the module PCB 208 for connecting to other components in the in-vehicle-sensing module 112.

The SoM 204 includes several components on one or more discreet modules or printed circuit boards. In the illustrated embodiment, the SoM 204 is configured as a single printed circuit board on which the several components are arranged. In particular, the SoM 204 includes at least a controller or control electronics having a processor and associated memory. It will be recognized by those of ordinary skill in the art that a "processor" includes any hardware system, hardware mechanism, or hardware component that processes data, signals or other information. The processor may include a system with a central processing unit, graphics processing units, multiple processing units, dedicated circuitry for achieving functionality, programmable logic, or other processing systems. The memory may be of any type of device capable of storing information accessible by the processor, such as a memory card, ROM, RAM, hard drives, discs, flash memory, or any of various other computer-readable medium serving as data storage devices, as will be recognized by those of ordinary skill in the art. The memory is configured to store program instructions that, when executed by the processor, enable the in-vehicle sensing module 112 to perform various operations, including monitoring the cabin 108 of the shared vehicle 102, as described below.

The SoM 204 may also include one or more sensors 116 integrated directly thereon. The SoM 204 may include, for example at least one temperature and/or humidity sensor, and a microphone integrated onto the printed circuit board. In further embodiments, the SoM 204 may also include an accelerometer, a gyroscope, a transceiver, and/or other sensors and electronics components.

The SoM 204 is arranged on and electrically connected to a module printed circuit board (PCB) 208. The module PCB 208 is operably connected to the vehicle battery 136 so as to receive electrical power from the vehicle battery 136. The module PCB 208 also includes power supply electronics that convert the received power, for example 12V power, to a lower voltage, for instance 3V, to power the components in the in-vehicle sensing module 112. The module PCB 208 is configured as a compact board to enable the in-vehicle sensing module 112 to have a small footprint. In one embodiment, the module PCB 208 is between approximately 5 and approximately 7 inches wide and between approximately 1.5 and approximately 2.5 inches long. In another particular embodiment, the module PCB 208 is approximately 6 inches wide and approximately 2 inches long.

Additionally, the module PCB 208 includes interfaces, headers, and/or connectors for communicating with sensors that are contained within or integrated within the in-vehicle sensing module 112, such as, for example, the camera 212 and particle sensor 216. Furthermore, the module PCB 208 has interfaces, headers, and/or connectors for communicating with additional sensors, for example the external sensor package discussed below, that are situated elsewhere in the vehicle 102 outside of the enclosure of the in-vehicle sensing module 112. The interfaces, headers, and/or connectors may connect to a plurality of communication buses, which may for example take the form of one or more $I^2C$ (Inter-Integrated Circuit) buses, $I^2S$ (Inter-IC Sound) buses, USB (Universal Serial Bus) buses, and/or CAN (Controller Area Network) buses. Accordingly, the module PCB 208 may include suitable bus controllers for communicating with the sensors via the communication buses.

The module PCB 208 further includes one or more radio transceivers, including at least a wireless telephony transceiver 232 configured to communicate with the Internet via wireless telephony networks, such as, for example, Global System for Mobiles ("GSM"), Code Division Multiple Access ("CDMA"), and/or Long-Term Evolution ("LTE") networks. Additionally, the radio transceivers of the module PCB 208 may further include a Bluetooth® or Wi-Fi transceiver configured to communicate locally with a smartphone or other smart device in the possession of the passenger or driver using the vehicle 102, or with the external sensor package. The radio transceivers of the module PCB 208 may include corresponding antennas, as well as any processors, memories, oscillators, or other hardware conventionally included with radio communications modules. In the illustrated embodiment, the wireless telephony transceiver is operably connected to two flexible antennas 236, 240 via the module PCB 208. The antennas 236, 240 may be, for example, 4G wide band antennas configured to receive and transmit at frequencies of between approximately 698 MHz and 3 GHz, though the reader should appreciate that other desired antennas may be used in other embodiments.

The module PCB 208 may also include additional sensors and electronics components. In addition, the reader should appreciate that any or all of the sensors and electronic components described as being included on the module PCB 208 may be instead arranged on the SoM 204. Likewise, any or all of the sensors and electronic components described as being included on the SoM 204 may instead be arranged on the module PCB 208.

The camera 212 of the in-vehicle sensing module 112 is mounted on a camera PCB 248, which is operably connected to the module PCB 208 for communication with the SoM 204 via, for example, a ribbon cable 252. The camera 212 further includes a camera lens 256 (FIG. 3) that is directed through a lens opening 260 in the lower housing 224 and is configured to capture images of the vehicle cabin 108. The camera 212 includes an image sensor, for example a CCD (charge coupled device) or a CMOS (complementary metal-oxide-semiconductor), configured to capture images in optical and/or infrared wavelengths.

Referring back to FIG. 2, the particle sensor 216 of the in-vehicle sensing module 112 is arranged beneath the module PCB 208 and is mounted to the lower housing 224 by a sensor cover 268. Additionally, the particle sensor 216 is operably connected to the module PCB 208 via a particle sensor connector 272, for example a ribbon cable, to receive electrical power from the module PCB 208 and communicate with the SoM 204 via the module PCB 208. The particle sensor 216 includes an intake opening 276, which is aligned with a particle sensor opening 280 defined in the lower housing 224, to enable ambient air in the cabin 108 to pass directly into the particle sensor 216. As discussed below, the particle sensor 216 is configured to sense particulate concentrations in the ambient air and transmit electronic signals corresponding to the detected particulate concentrations to the SoM 204, which determines whether smoke or vapor is present in the cabin 108.

The in-vehicle sensing module 112 of the illustrated embodiment has two LED arrangements 220, one of which is located on each side of the camera 212. Each LED arrangement 220 includes two LEDs 288, an LED board 292, and an LED cover 296, which mounts the LED board 292 and the LEDs 288 to the lower housing 224. The LED board 292 is operably connected to the module PCB 208 so as to receive electrical power from the module PCB 208 and communicate with the SoM 204 via the module PCB 208. Each LED 288 is arranged so as to project light through an LED opening 300 defined in the lower housing 224. The LEDs 288 may be configured to project white light, infrared light, or light of another suitable wavelength into the cabin 108 of the vehicle 102. In one particular embodiment, one LED 288 of the LED arrangement 220 generates white light, while the other LED 288 produces infrared light.

The LEDs 288 are operated by the processor in the SoM 204 to illuminate the cabin 108 of the vehicle 102 so that the camera 212 can capture an image of sufficient quality. Additionally, the LEDs 288 of the LED arrangements 220 may be arranged in a common plane on the lower surface of the lower housing 224, thereby enabling the light produced by the LEDs 288 to illuminate the cabin 108 evenly.

The module PCB 208 is connected to the SoM 204 and the heatsink 200 via a plurality of fasteners 304, each of which extends upwardly through the module PCB 208, a corresponding spacer 308, the SoM 204, and into a threaded opening (not shown) in the heatsink 200. The heatsink 200, SoM 204, and module PCB 208 are therefore configured as a self-contained unit. The self-contained unit of the heatsink 200, SoM 204, and module PCB 208 is affixed to the lower housing 224 via a plurality of fasteners 312 that pass downwardly through corresponding openings in the heatsink 200 and module PCB 208, into threaded openings in the lower housing 224.

The camera 212 is affixed to the lower housing 224 by a plurality of fasteners 316 that pass downwardly through the camera PCB 248 and into corresponding threaded openings in the lower housing 224. Similarly, the particle sensor 216 is mounted to the lower housing 224 by a plurality of fasteners 320 that pass through the particle sensor cover 268 and into corresponding threaded openings in the lower housing 224 to clamp the particle sensor 216 between the particle sensor cover 268 and the lower housing 224. Each LED arrangement 220 is likewise mounted to the lower housing 224 by a plurality of fasteners 324 that pass through the LED cover 296 and the LED board 292 into corresponding threaded openings in the lower housing 224, thereby clamping the respective LED board 292 and LEDs 288 between the LED cover 296 and the lower housing 224.

As such, the camera 212, particle sensor 216, and LED arrangements 220 are mounted to the lower housing 224 independently of the self-contained unit of the heatsink 200, SoM 204, and module PCB 208. In other words, the fasteners 316, 320, 324 that fasten the camera 212, particle sensor 216, and LED arrangements 220 to the lower housing 224 do not interact with the heatsink 200, SoM 204, or module PCB 208. Likewise, the fasteners 312 that fasten the heatsink 200, SoM 204, and module PCB 208 to the lower housing 224 do not interact with the camera 212, particle sensor 216, or LED arrangements 220. The heatsink 200, SoM 204, and module PCB 208 are therefore arranged so as to be physically spaced apart from the camera 212, particle sensor 216, and LED arrangements 220. As a result, heat produced by the electronic components in the module PCB 208 and SoM 204 is not conducted downwardly into the camera 212, particle sensor 216, or LED arrangements 220, and is instead conducted upwardly through the heatsink 200 and out of the top of the in-vehicle sensing arrangement 112. Consequently, the in-vehicle sensing arrangement 112 provides effective heat management so as to prevent or minimize overheating of the components in the in-vehicle sensing arrangement 112.

Figure 3:
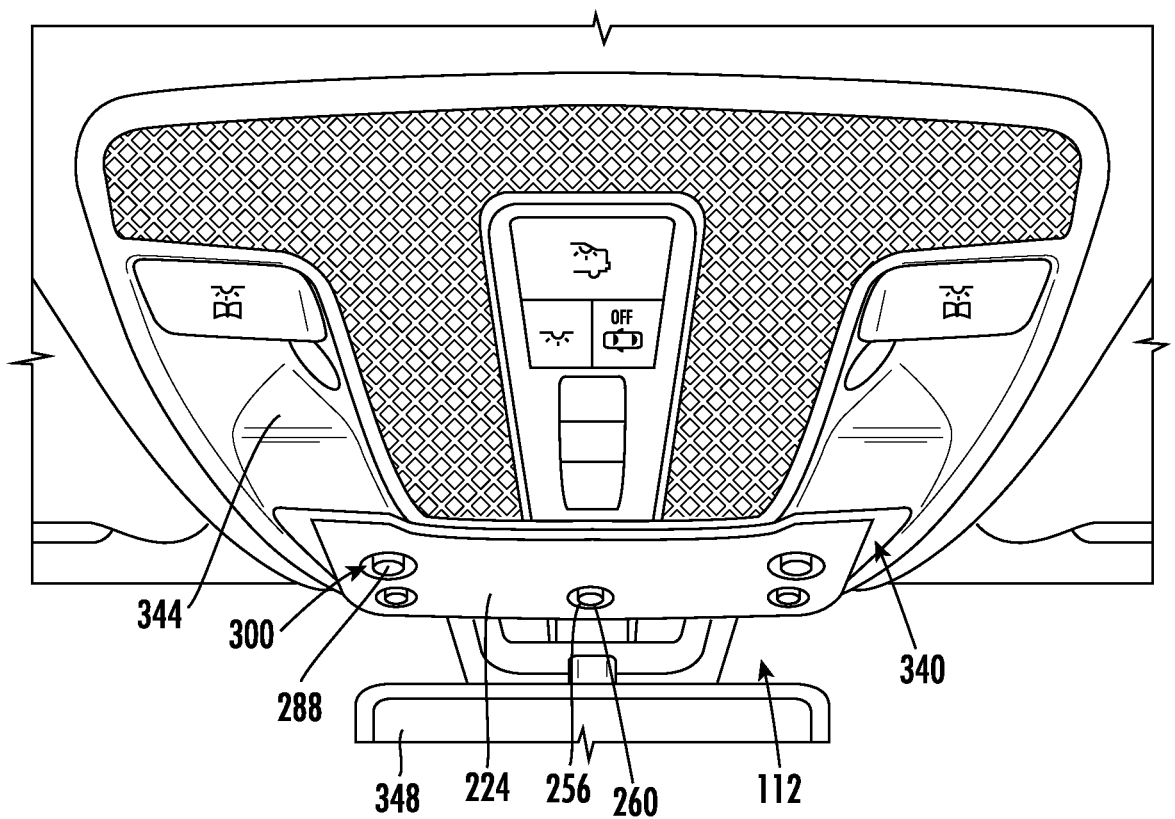
FIG. 3 shows photo of the in-vehicle sensing module of FIG. 2 arranged in a roof bezel of a vehicle.

As seen in FIGS. 2 and 3, the in-vehicle sensing module 112 is configured as a self-contained package. As a result, the in-vehicle sensing module 112 is easily installed into existing vehicles as a retrofit. The lower housing 224 may be modified to conveniently fit in different vehicles, while the configuration of the heatsink 200, SoM 204, module PCB 208, camera 212, particle sensor 216, and LED arrangements 220 can be the same across different configurations of the lower housing 224.

As depicted in FIG. 3, in one particular embodiment, the in-vehicle sensing module 112 is configured to be received in a receptacle 340 in the roof bezel 344 of the vehicle 102. More particularly, the in-vehicle sensing module 112 may be arranged rearward of the rearview mirror 348, and the receptacle 340 may be a sunglasses holder. Since many vehicles have a sunglasses holder in the roof bezel 344, the in-vehicle sensing module 112 can be conveniently adapted to a variety of different vehicles with minimal modification of the arrangement of the in-vehicle sensing module 112 or the vehicle 102. For example, the in-vehicle sensing module 112 may be configured such that the lower housing 224 aesthetically matches the roof bezel 344 of the vehicle 102, as illustrated in FIG. 3.

Figure 4:
FIG. 4 shows a photo captured by the in-vehicle sensing module of FIG. 3 in which left behind objects are marked with boxes.
Figure 5:
FIG. 5 shows a photo captured by the in-vehicle sensing module of FIG. 3 in which dirt on the floor of the vehicle is marked with boxes.
Figure 6:
FIG. 6 shows a photo captured by the in-vehicle sensing module of FIG. 3 in which debris on the floor and seats of the vehicle is marked with boxes.
Figure 7:
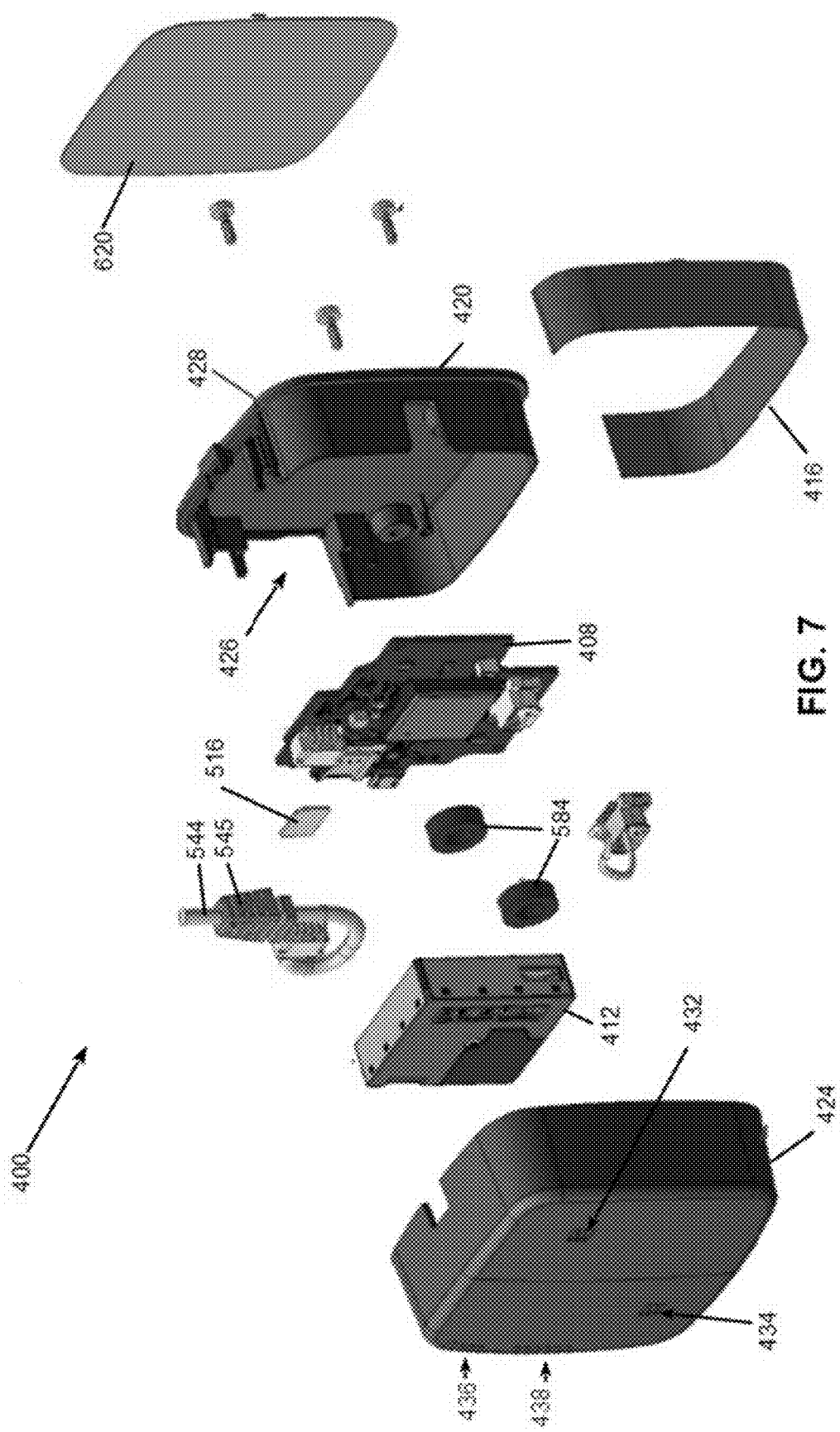
FIG. 7 shows an exploded view of another in-vehicle sensing module.

Moreover, as seen in FIGS. 4-6, by mounting the in-vehicle sensing module 112 rearward of the rearview mirror 348, the camera 212 has a direct view of the floors and seats in the cabin 108 of the vehicle 102. As a result, the in-vehicle sensing module 112 enables suitable visual coverage of the vehicle with only the one camera 212.

Furthermore, in the configuration of the in-vehicle sensing module 112 illustrated in FIGS. 2 and 3, the particle sensor opening 280 is arranged in the front portion of the lower housing 224 relative to the vehicle. The particle sensor opening 280 is therefore located, as viewed by the passengers, behind the main or lowered portion of the lower housing 224. As a result, the particle sensor opening 280 is generally obscured from view by the passengers of the vehicle 102. The passengers are therefore unlikely to be aware of the location of the particle sensor opening 280, and are thus unlikely to tamper with the particle sensor opening 280 in an attempt to avoid detection of smoking or vaping in the vehicle cabin 108.

Additionally, since the intake opening 276 of the particle sensor 216 is aligned with the particle sensor opening 280 of the lower housing 224, ambient air can pass directly from the cabin 108 into the intake opening 276. Accordingly, the ambient air does not disperse through the interior of the lower housing 224 where the ambient air could be diluted or heated by the components in the lower housing 224.

As noted above, the in-vehicle sensing module 112 may be connected to sensors located outside of the enclosure of the in-vehicle sensing module 112. As an example, the gyroscope/accelerometer module 122 may be attached to the chassis of the vehicle 102 to provide improved sensitivity to small damage to the vehicle 102. In one embodiment, the gyroscope/accelerometer module 122 also includes an additional microphone separate from the microphone in the SoM 204. The gyroscope/accelerometer module 122 may be operably connected to the in-vehicle sensing module 112 by a cable or wired connection, or it may be operably connected to the in-vehicle sensing module 112 via a known wireless connection method.

In some embodiments, the in-vehicle sensing module 112 may further include various indicator lights, user interfaces, speakers, or the like for locally conveying or receiving information to or from the passengers of the vehicle.

Operation of the in-Vehicle Sensing System Having a Camera

In some embodiments, the in-vehicle sensing module 112 of FIGS. 2-3 is configured to detect whether a passenger is smoking within the cabin 108 of the vehicle 102 based on sensor data received from smoke detectors or other air-quality/particle sensors, which may be provided and/or accessed at a predetermined rate (e.g., once per second). In one embodiment, the in-vehicle sensing module 112 executes a smoke detection algorithm to monitor a curve of particulate matter concentrations detected by, for example, the particle sensor 216, over time and compares the monitored particulate matter concentrations to reference data. In case of a smoke detection event, the in-vehicle sensing module 112 may also operate the camera 212 to take a photo of the cabin 108 of the vehicle 102 and/or to generate an audible alert in the vehicle.

Additionally, some embodiments of the in-vehicle sensing module 112 are configured to detect whether the vehicle 102, in particular a car body of the vehicle 102, has incurred damage during based on sensor data received from a gyroscope, acceleration sensor, vibration sensor and/or a microphone, e.g. from the gyroscope/accelerometer module 122. In one embodiment, the in-vehicle sensing module 112 executes an appropriate learning algorithm (an artificial neural network) to collect and analyze the sensor data to detect that a small damage has occurred. In one embodiment, based on the sensor data received from the sensors, the in-vehicle sensing module 112 detects the location on the vehicle at which the damage occurred (e.g., front left) and classifies a grade of damage (e.g., hard or minor), based on the data received from the sensors.

In some embodiments, the in-vehicle sensing module 112 is configured to detect whether objects have been left behind by passengers of the vehicle, such as phones, keys, or glasses. In one embodiment, the in-vehicle sensing module 112 operates the LEDs 288 to illuminate the cabin 108 and the camera 212 to capture a sample photo after a ride is finished and the user has left the car. The in-vehicle sensing module 112 then executes an appropriate algorithm to analyze the sample photo and determine optimal parameters (e.g., exposure, gain, gamma, etc.) for subsequent photos. Directly afterwards, the in-vehicle sensing module 112 operates the LEDs 288 and camera 212 to capture a set of photos using the determined parameters to get the best results and form a high dynamic range (HDR) photo using the set of photos. The in-vehicle sensing module 112 executes an appropriate algorithm to analyze the HDR photo to detect lost or left behind objects in the vehicle 102. The in-vehicle sensing module 112 marks the lost or left behind objects in the HDR photo, such as with boxes as shown in FIG. 4, and also lists the objects in metadata. In one embodiment, the in-vehicle sensing module 112 distinguishes and classifies the lost or left behind objects and includes these classifications in the metadata. In this way, a user can be informed immediately in case of detecting a lost or left behind object. Additionally, an operator can analyze the HDR photo and correct it in case of any doubts.

In some embodiments, the in-vehicle sensing module 112 is configured to detect whether the cabin 108 of the vehicle is clean or dirty. Dirt can assume several forms including dust, different varieties of soil, or even debris, scattered pieces of rubbish or remains. Common examples include sand or grass on the floor of the cabin 108, as shown in FIG. 5, and crumbs or other debris on the floor or seats of the cabin 108, as shown in FIG. 6. In one embodiment, the in-vehicle sensing module 112 operates the LEDs 288 to illuminate the cabin 108 and the camera 212 to capture a sample photo and then a HDR photo, as described above for detecting lost or left behind objects. The in-vehicle sensing module 112 executes an appropriate algorithm to analyze the HDR photo to detect dirt or debris in the vehicle 102. The in-vehicle sensing module 112 marks the dirt or debris in the HDR photo, such as with boxes as shown in FIG. 5 and FIG. 6, and also lists the dirt or debris in metadata. In one embodiment, the in-vehicle sensing module 112 classifies the detected dirt or debris (e.g., removable/not removable, trash, dangerous, liquid, etc.) and includes these classifications in the metadata. In this way, an operator can be informed immediately in case of a dirty vehicle can decide how to proceed (e.g., car has to be cleaned, repaired, etc.). Additionally, an operator can analyze the HDR photo and correct it in case of any doubts.

In at least one embodiment, the in-vehicle sensing module 112 is configured to transmit sensor data and processing results to a remote server backend. In particular, the in-vehicle sensing module 112 operates one or more transceivers (e.g. the wireless telephony transceiver 232) thereof to transmit raw sensor data, enriched or annotated sensor data, and/or detected event data with relevant photos or the like to the remote server backend. In one embodiment, the remote server backend is associated with or accessible by an operator of a shared vehicle service for which the vehicle 102 is utilized. In this way, operators can evaluate the data and events on the backend and react in an appropriate way. Alternatively, remote server backend may be associated with an OEM of the vehicle 102 or with some other interested party.

In-Vehicle Sensing System with an Environmental Sensor

Another embodiment of an in-vehicle sensing module 400 is depicted in FIGS. 7-12. The in-vehicle sensing module 400 of FIGS. 7-12 may be used in place of the in-vehicle sensing module 112 described above. The in-vehicle sensing module 400 is configured without a camera, however, so as to enable the in-vehicle sensing module 400 to be compact and easily installable on a vehicle windshield without obstructing the driver's view.

The in-vehicle sensing module 400 includes a housing 404, which supports a PCB 408, a particle sensor 412, and a flexible antenna 416. The housing 404 includes a base 420 and a cover 424, best seen in FIGS. 7-9, which jointly define an interior space 426 in which the PCB 408 and the particle sensor 412 are arranged. The base 420 and cover 424 may be formed as plastic injection-molded components, though the reader should appreciate that the base 420 and cover 424 may be formed of any desired material.

The base 420 has a sidewall 428 that extends around a portion of the exterior circumference of the base 420 so as to at least partially define the interior space 426. The base 420 further defines a plurality of projections that serve to aid in locating and mounting the various components arranged in the interior space 426. One of the projections is configured as a separator 430, which, as will be discussed in further detail below, separates an inlet region 454, from which the particle sensor 412 collects air, from the remainder of the interior space 426.

The interior space 426 is substantially enclosed by the housing 404 so as to reduce the flow of air and any other contaminants into and out from the interior space 426. In one particular embodiment, exchange of air into and out from the interior space 426 is enabled only by a plurality of groups of openings 432, 434, 436, 438. Two of the groups of openings 432, 434 open into the interior of respective cylindrical projections 440, 442, which project from the top of the cover 424 into the interior space 426. In particular, as will be discussed in detail below, the openings 432, 434 provide a substantially uninterrupted path for sound waves to travel from the cabin 108 to the microphones 580 arranged on the PCB 408.

Another group of openings 436 allows ambient air to be pulled into an inlet 450 of the particle sensor 412, while the group of openings 438 enables air expelled from an outlet 456 of particle sensor 412, as well as the air in the remainder of the interior space 426, to exit the interior space 426. In addition, the cover 424 includes two separators 444, 446 extending into the interior space 426 between the openings 436, 438. The two separators 444, 446 cooperate with the separator 430 of the base 420 to substantially or completely isolate the openings 436, 438, from one another within the interior space 426, and to substantially or completely isolate the inlet region 454 from the remainder of the interior space 426. As used herein, substantially isolated means there are no gaps that connect the inlet region 454 and the remainder of the interior space 426, or connecting the openings 436, 438, with an area perpendicular to a nominal direction of airflow of greater than 10 mm$^2$. In some embodiments, there are no gaps connecting the inlet region 454 and the remainder of the interior space having an area perpendicular to a nominal direction of airflow of greater than 5 mm$^2$, while in other embodiments there are no gaps with an area of greater than 3 mm$^2$.

The cover 424 also includes a sidewall 448 that extends circumferentially entirely around the cover 424 so as to enclose the interior space 426. The sidewall 448 surrounds the sidewall 428 of the base 420 in such a way that the flexible antenna 416 is interposed between the two sidewalls 428, 448. In the illustrated embodiment, the flexible antenna 416 extends entirely around two sides of the sidewall 448, and partially around the other two sides of the sidewall 448.

Figure 8:
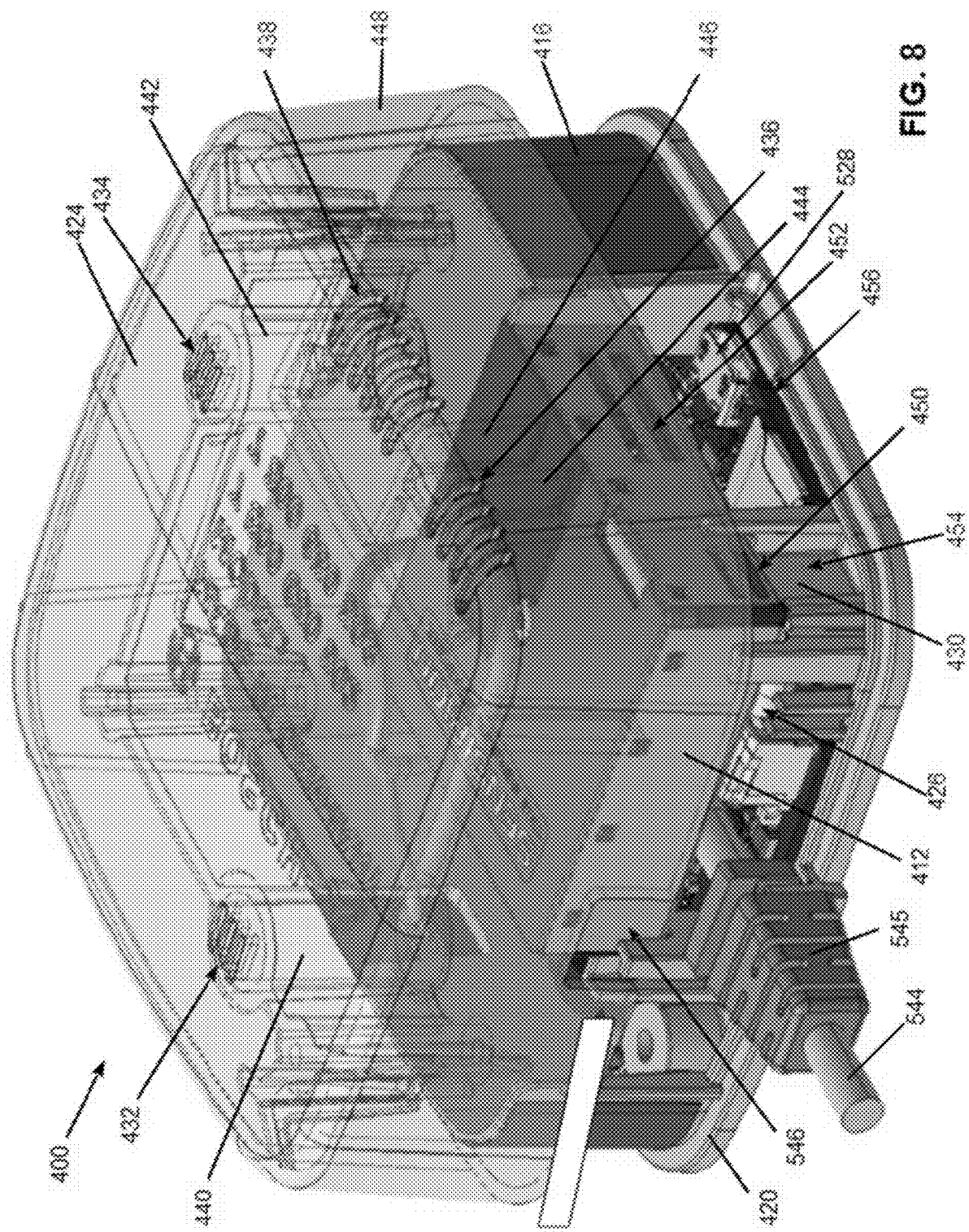
FIG. 8 shows a perspective view of the in-vehicle sensing module of FIG. 7 with the housing cover shown transparent and partially removed from the housing base.

As best seen in FIG. 8, the particle sensor 412 has an inlet 450 and an outlet 452 arranged on the same side of the particle sensor 412. The inlet 450 and outlet 452 are both arranged on a side of the particle sensor that is adjacent to the sidewall 448 so that only a relatively small volume of air is present between the inlet 450 and outlet 452 and the sidewall 448. The particle sensor 412 has a fan configured to produce airflow that draws air into the inlet region 454 and into the inlet 450 of the particle sensor 412.

In the illustrated embodiment, the inlet region 454 encompasses a relatively small portion of the interior space 426. In particular, in one embodiment, the volume of the inlet region 454 is less than 10% of the overall volume of the interior space 426. In other embodiment, the volume of the inlet region 454 is less than 5%, less than 3%, or less than 2% of the overall volume of the interior space. Since the inlet region is relatively small compared to the overall volume of the interior space 426, the air drawn into the inlet region 454 has a small volume in which to disperse once being drawn into the inlet region 454. As a result, the majority of the air drawn into the inlet region 454 proceeds directly from the openings 436 into the inlet 450 of the particle sensor 412. The in-vehicle sensing module 400 therefore enables accurate sensing of the particulate matter in the air of the vehicle cabin 108.

The particle sensor 412 is configured to sense particulate matter concentrations in the ambient air of the cabin 108. In particular, the particle sensor 412 is at least configured to detect particulate matter having sizes or masses associated with smoke and, in particular, with tobacco smoke and/or marijuana smoke, but may also detect particulate matter associated with other airborne particles or water vapor. The particle sensor 412 processes the air received in the inlet 450 to analyze the air for the presence and size of particles, and then expels the air through the outlet 452 into the outlet region 456. The air expelled into the outlet region 456 disperses through the interior space 426 and exits the housing 404 via the openings 438.

Figure 10:
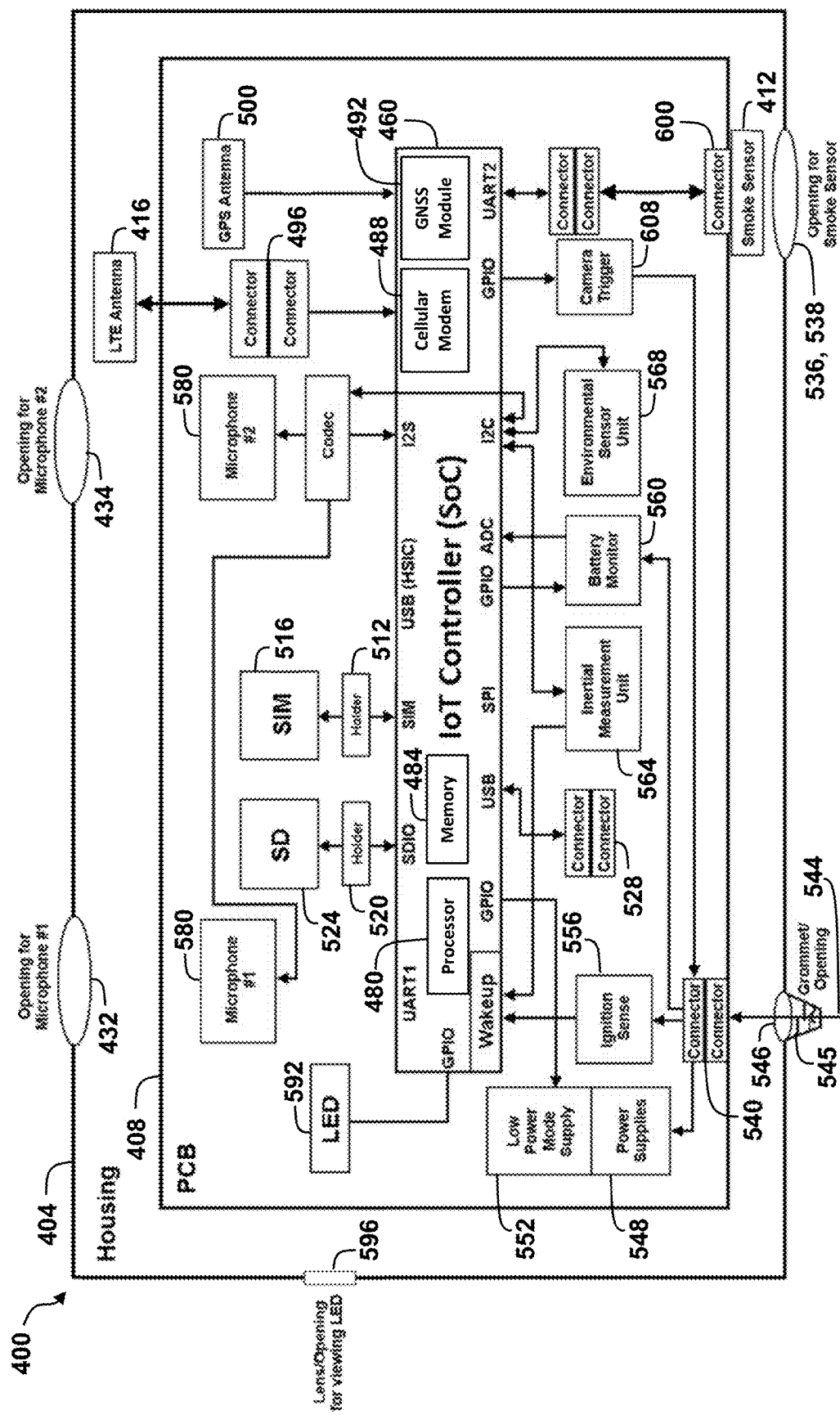
FIG. 10 shows a schematic view of the components of the in-vehicle sensing module of FIG. 7.
Figure 11:
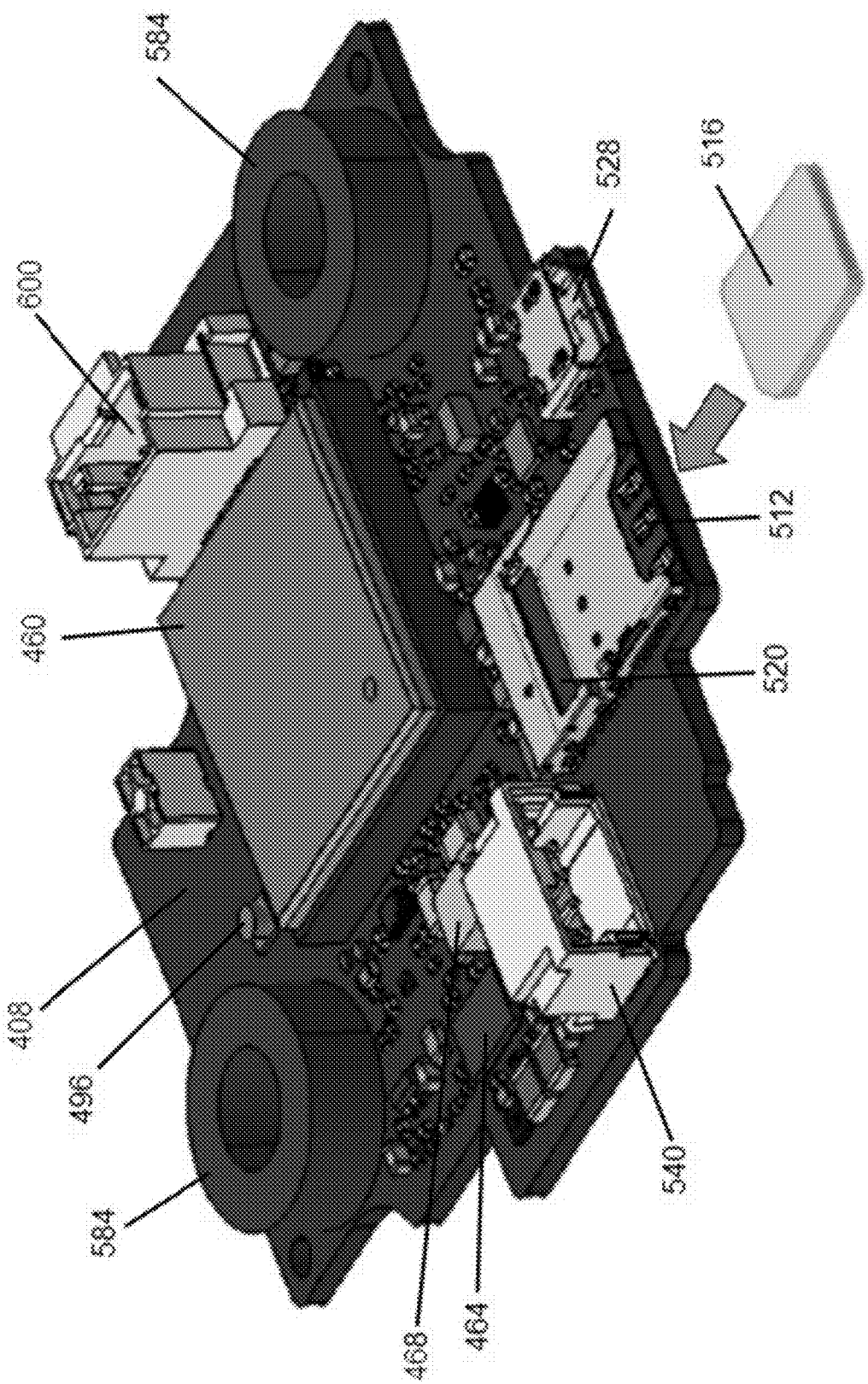
FIG. 11 shows a perspective view of the circuit board of the in-vehicle sensing module of FIG. 7.

With reference now to FIGS. 10 and 11, the PCB 408 supports and electrically interconnects a plurality of electrical components, including at least a controller 460, an inertial measurement unit ("IMU") sensor 464, and a environmental sensor 468. The IMU sensor 464 includes one or more gyroscope sensors and one or more accelerometers. In one particular embodiment, the IMU sensor 464 may be a 6-axis sensor having a tri-axial gyroscope and a tri-axial accelerometer. The IMU sensor 464 is operably connected to the controller 460 so as to transmit information sensed by the IMU sensor 464 indicative of speed and movement of the in-vehicle sensing module 400. The information sensed by the IMU sensor 464 is used by the controller 460 to determine whether the vehicle has been involved in a collision, and the severity of any detected collision events.

The environmental sensor 468 is configured to analyze the air inside the interior space 426 to determine one or more properties of the air in the vehicle cabin 108. In one particular embodiment, the environmental sensor 468 is configured to detect properties indicative of the air quality in the cabin such as relative humidity, barometric pressure, temperature, and presence of organic compounds, more particularly volatile organic compounds ("VOCs"). Accordingly, the environmental sensor 236 includes a variety of individual sensors integrated into a single package. However, it should be appreciated that individual discreet sensors may alternatively be provided, including a VOC sensor, a humidity sensor, a barometric pressure sensor, and a temperature sensor. The environmental sensor 468 is operably connected to the controller 460 so as to transmit signals indicative of the sensed parameters to the controller 460 via, for example, an I$^2$C connection.

The controller 460 includes at least a processor 480 and associated memory 484. As noted above, it will be recognized by those of ordinary skill in the art that a "processor" includes any hardware system, hardware mechanism or hardware component that processes data, signals or other information. Accordingly, the processor 480 may include a system with a central processing unit, graphics processing units, multiple processing units, dedicated circuitry for achieving functionality, programmable logic, or other processing systems. The memory 484 may be of any type of device capable of storing information accessible by the processor, such as a flash memory card, ROM, RAM, hard drives, discs, or any of various other computer-readable media serving as volatile or non-volatile data storage devices, as will be recognized by those of ordinary skill in the art. The memory 484 is configured to store program instructions that, when executed by the processor 480, enable the in-vehicle sensing module 400 to perform various operations, including monitoring the cabin 108 of the shared vehicle 102, as described below.

In the illustrated embodiment, the controller 460 takes the form of an Internet of Things (IoT) controller 460, which has integrated features and functionalities beyond that of a generic multi-purpose controller. As such, in the illustrated embodiment, the IoT controller 460 is configured as a system on a chip (SoC), which is arranged on the PCB 408. Alternatively, the IoT controller 460 may be equivalently configured as a system on a module (SoM) in which the sub-components thereof are arranged on at least one discreet PCB, which is connected to the PCB 408 by a cable and/or a module connector. In either case, the IoT controller 460 includes integrated features and functionalities beyond the processor 480 and memory 484.

In the illustrate embodiment, the IoT controller 460 further includes a radio communication module, which is a cellular telephony modem 488 in the illustrated embodiment, that is operably connected to an antenna connector 496 on the PCB 408. The antenna connector 496 is connected to the flexible antenna 416, which is configured to improve the cellular reception of the in-vehicle sensing module 400. The cellular telephony modem 488 is configured to communicate with the Internet in conjunction with the antenna 416 via wireless telephony networks, such as, for example, GSM, Code CDMA, and/or LTE networks. The reader should appreciate that, while the illustrated embodiment depicts the cellular telephony modem 488 as being integrated with the controller 460, in other embodiments the cellular telephony modem 488 may be arranged on the PCB 408 separate from the controller 460.

The PCB 408 further includes a subscriber identity module ("SIM") card receptacle 512, which is configured to accommodate a SIM card 516. The SIM card receptacle 512 is operably connected to the controller 460, and more specifically to the cellular telephony modem 488, so as to provide identifying information to enable the cellular telephony modem 488 to access the wireless telephony network, as is generally known in the art.

In some embodiments, the IoT controller 460 advantageously provides integrated Global Navigation Satellite System (GNSS) functionality. To this end, the IoT controller 460 comprises a GNSS receiver as well as any other processors, memories, oscillators, or other hardware conventionally included in a GNSS module 492. The GNSS receiver is configured to receive signals from GNSS satellites from which location data can be determined. The GNSS receiver is configured to support one or more of, for example, GPS, GLONASS, BeiDou, and Galileo, or any other GNSS. The GNSS receiver is connected to a GNSS antenna 500 to enable reception of the GNSS signals. In the illustrated embodiment, the GNSS antenna 500 is arranged in or on the PCB 408, but can alternatively be arranged separately inside or outside the housing 404. It should be appreciated that in alternative embodiments, a discreet GNSS module can be provided on the PCB 408 separate from the controller 460.

In some embodiments (not shown), the IoT controller 460 may further include integrated Bluetooth® and/or Wi-Fi® transceivers configured to communicate locally with a smartphone or other smart device in the possession of the passenger or driver using the shared vehicle 102. Likewise, in some embodiments, discreet Bluetooth® and/or Wi-Fi® transceivers can be provided on the PCB 408 separately from the controller 460.

In some embodiments, the IoT controller 460 advantageously comprises a variety of integrated data/peripheral interfaces for operably connecting with a variety of additionally components of the in-vehicle sensing module 400, including general-purpose input/output (GPIO), Serial Peripheral Interface (SPI), Inter-Integrated Circuit ($I^2C$ or I2C), Inter-IC Sound ($I^2S$ or I2S), Secure Digital Input Output (SDIO), Universal Serial Bus (USB), USB High Speed Inter-Chip (HSIC), and universal asynchronous receiver-transmitter (UART). In this way, the IoT controller 460 provides easy compatibility with a variety of external sensors that might be available within the shared vehicle 102, as well as providing compatibility with a variety of configurations of integrated sensors.

In addition, the PCB 408 may include a removable storage medium holder 520, for example a secure digital ("SD") card reader or the like that is configured to accommodate and communicate with a removable memory storage device 524, for example a secure digital (SD), SD High Capacity (SDHC), or SD Extended Capacity (SDXC) memory card, as well as any equivalent type of removable memory card or other non-volatile memory technology. The removable storage medium holder 520 may be connected to the controller 460 via, for example, a SDIO interface. The controller 460 may be configured to write the metadata processed from the sensor data to the removable memory storage device 524, and to read instructions, program code, or other information from the removable memory storage device 524.

In addition, the PCB 408 may, in some embodiments, also include an external device connector 528 connected to the controller 460. The external device connector 528 enables an external computing device, such as a diagnostic tool or the like, to be temporarily connected to the in-vehicle sensing module 400 to read or receive data from the in-vehicle sensing module 400. The external device connector 528 may, for example, take the form of a USB connector (e.g. USB-A, USB-C, micro-USB, etc.) or the like, configured to enable wired communication between the controller 460 and the external computing device.

In addition, the PCB 408 includes an input/output ("I/O") connector 540, which is connected to an external cable 544 that connects to the I/O connector 540 and exits the housing 404 via an opening 546 defined therein. In one embodiment, the external cable 544 includes a grommet 545 arranged at the opening 546, which is configured to attach the external cable 544 to the housing 404 at the opening 546 to provide strain relief. The external cable 268 is configured to connect with one or more vehicle interfaces, busses, or systems of the shared vehicle 102, at least including the power line 140, via one or more wire harnesses, or equivalent, so as to receive a vehicle battery voltage 547 (e.g. 12V) from the vehicle battery 136. Additionally, in at least some embodiments, the external cable 544 is configured to connect with the one or more communication buses 124 so as to receive data from external sensors and/or from the vehicle ECU 128. In one particular embodiment, the external cable 544 is connected to the overhead bezel of the vehicle 102. The reader should appreciate that, in some embodiments, the PCB includes or is operably connected to a dedicated battery in place of the external cable 544 or as a secondary power source if the power supply from the vehicle is interrupted.

The I/O connector 540 is operably connected to power supply circuitry 548 of the PCB 408, configured to convert power from the vehicle battery 136 to suitable voltages for providing power to the controller 460 and other components of the in-vehicle sensing module 400. The power supply circuitry 548 also includes low power mode circuitry 552, which is configured to provide power only to a select subset of components of the in-vehicle sensing module 400 in a low power mode, to avoid draining the vehicle battery 136 when the vehicle is off.

The PCB 408 further includes ignition sensing circuitry 556 that is operably connected to the I/O connector 540 and to the controller 460. The ignition sensing circuitry 556 is configured to monitor the input voltage provided from the vehicle battery 136 to determine when the ignition of the vehicle 102 has been activated. The ignition sensing circuitry 556 then transmits an ignition signal to the controller 460. As will be discussed further below, in at least some embodiments, the in-vehicle sensing module 400 switches from a low power mode to an active state in response to the ignition signal. In other words, the ignition signal may act as a wakeup signal for the controller 460.

The PCB 408 further includes battery monitoring circuitry 560, which is operably connected to the controller 460 and the I/O connector 540 and functions to monitor the state of the vehicle battery. For instance, the battery monitoring circuitry 560 may be configured to monitor the voltage and current provided to the in-vehicle sensing module 400. In some embodiments, a power state of the in-vehicle sensing module 400 (e.g., off, on, low power mode, active mode) is controlled or changed by the controller 460 depending on the voltage and current sensed by the battery monitoring circuitry 560.

The PCB 408 also includes at least one microphone 580 operably connected to the controller 460. Each microphone 580 comprises any desired type of acoustic sensor configured to record sounds within the cabin 108. In one particular embodiment, each microphone 240 takes the form of a Micro-Electro-Mechanical Systems (MEMS) microphone mounted directly on the PCB 208.

In the illustrated embodiment, the PCB 408 includes two microphones 580 that are spaced apart from one another so as to record stereo audio in the cabin 108. Each microphone 480 is surrounded by an acoustic seal gasket 584, one end of which seals against the PCB 408. The inner circumferential surface of each acoustic seal gasket 584 seals against an associated one of the cylindrical projections 440, 442 on the interior side of the housing cover 420. The acoustic seal gaskets 584 therefore acoustically isolate the volume in which the microphones 580 are arranged so as to reduce interference in the sound transmitted through the openings 432, 434 and detected by the microphones 580.

In some embodiments, the in-vehicle sensing module 400 includes an indicator light (e.g. an LED) 592 mounted on the PCB 408 or the housing 404. The indicator light 592 is arranged so as to be visible through an opening 596 of the cover 424, and is configured to emit light that indicates an operating status of the in-vehicle sensing module 400.

Figure 9:
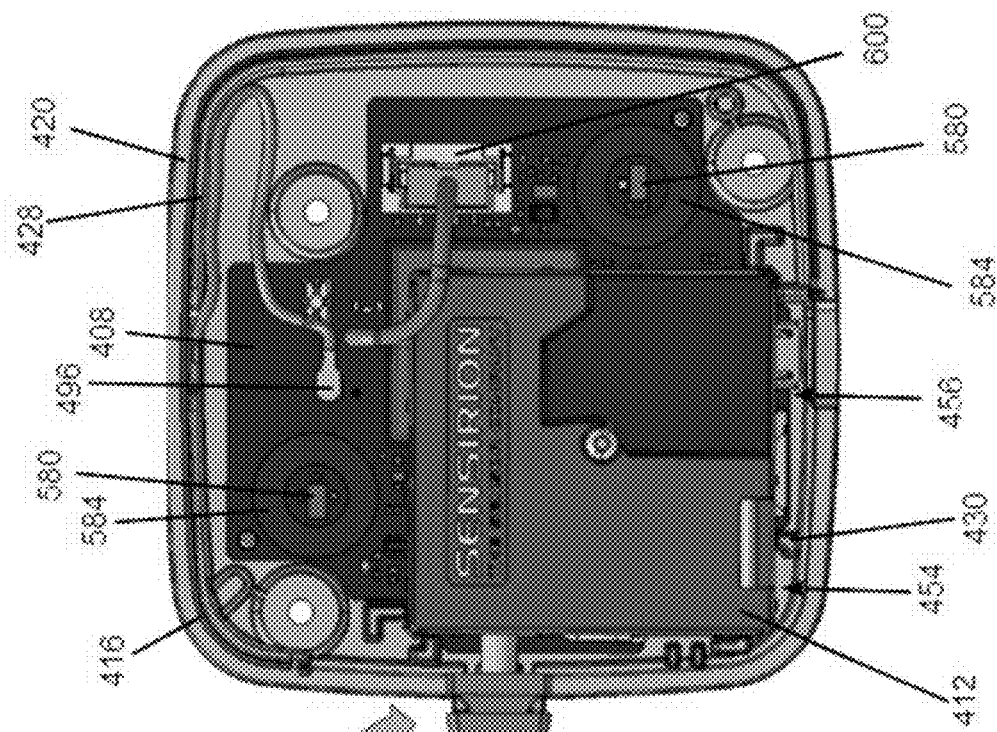
FIG. 9 shows a top view of the in-vehicle sensing module of FIG. 7 with the housing cover removed and inverted.
Figure 9:
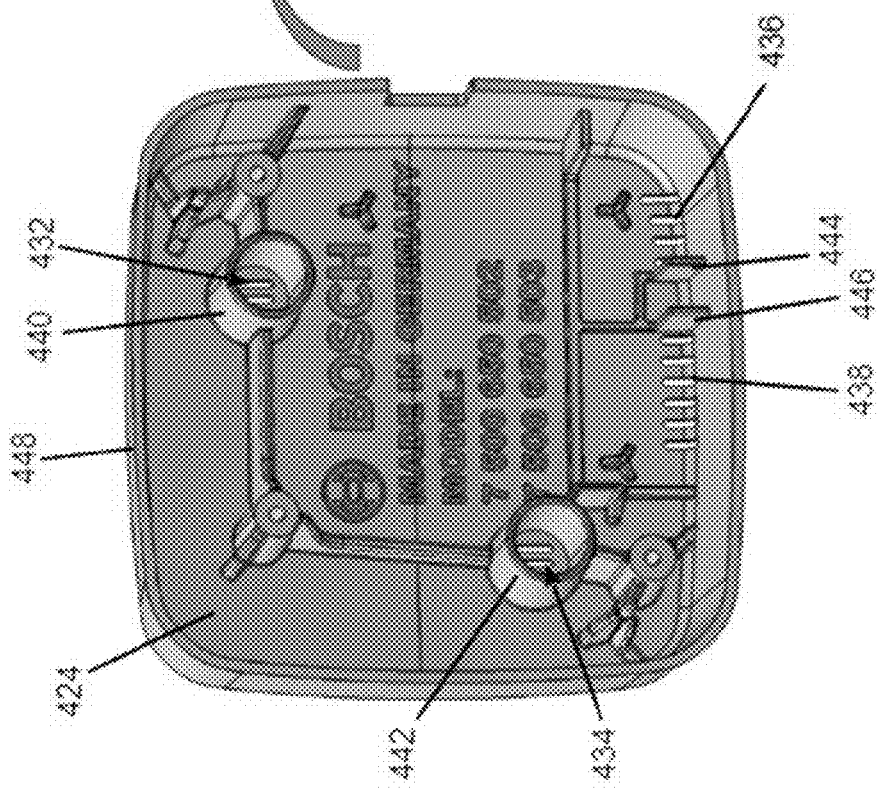

The PCB 408 also supports a particle sensor connector 600, seen in FIGS. 9 and 10, which is operably connected to the controller 460 via electrical connections in the PCB 408. The particle sensor connector 600 enables transfer of data between the controller 460 and the particle sensor 412, and enables the power supply circuitry to supply the particle sensor 412 with electrical power.

In some embodiments, the PCB further includes camera trigger circuitry 608. The controller 460 is configured to operate the camera trigger circuitry 608 to activate an external camera 612, which is arranged within the shared vehicle and configured to capture images of the cabin 108, to capture one or more pictures inside the vehicle cabin in a manner as described above. The controller 460 is configured to receive the captured images from the external camera 612 via the camera trigger circuitry 608 or via another data connection.

Figure 12:
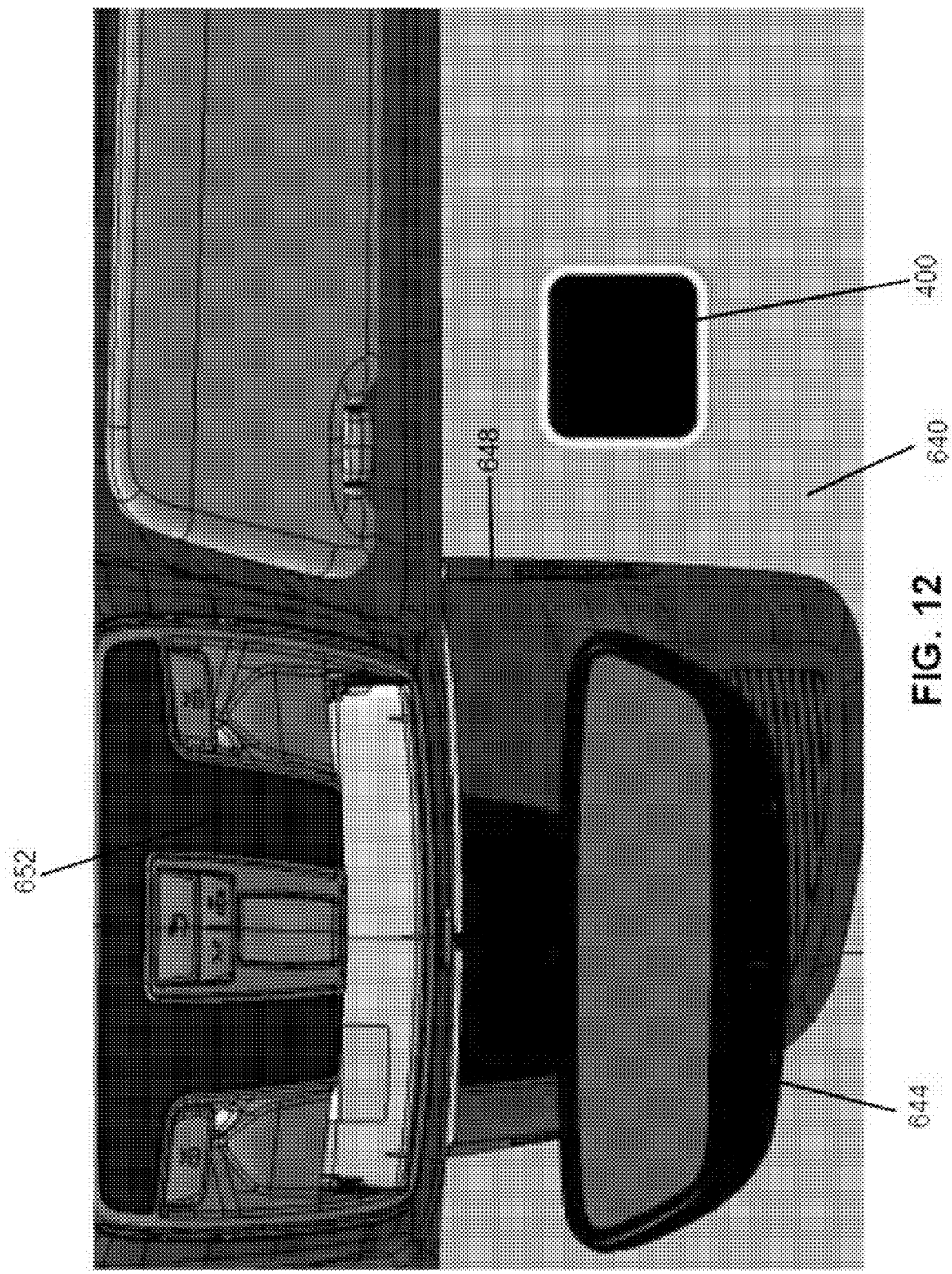
FIG. 12 shows a front view of the in-vehicle sensing module of FIG. 7 mounted on the windshield of a vehicle.

In the illustrated embodiment, as is seen in FIG. 12, the in-vehicle sensing module 400 is configured to be installed on the windshield 640 of the vehicle 102. The in-vehicle sensing module 400 therefore includes a double-sided adhesive pad 520 configured to affix the back side of the housing base 420 (i.e. the side opposite the interior space 426) to the windshield 640 of the vehicle. In some embodiments, the in-vehicle sensing module 400 is configured to be affixed to the windshield 640 on the side of the rearview mirror 644 opposite the driver side (i.e. to the right of the rearview mirror 644 in left-hand-drive vehicles). The in-vehicle sensing module 400 may be arranged between approximately 25 mm and 75 mm, or more particularly approximately 50 mm, from the top of the windshield 640, and between 25 mm and 75 mm, or more particularly approximately 50 mm, from the rearview mirror 644 or an exterior sensing module 648. This positioning enables the power supply cable 544 to be easily routed to the overhead bezel 652 without obstructing the driver's view.

Operation of the in-Vehicle Sensing Module with an Environmental Sensor

A variety of methods and processes are described below for operating the in-vehicle sensing module 400. In these descriptions, statements that a method, processor, and/or system is performing some task or function refers to a controller or processor (e.g., the controller 460 of the in-vehicle sensing module 400) executing programmed instructions stored in non-transitory computer readable storage media (e.g., the memory 484 of the controller 460 of the in-vehicle sensing module 400 or the removable memory storage device 524) operatively connected to the controller 460 or processor 480 to manipulate data or to operate one or more components in the vehicle monitoring system 100 or the in-vehicle sensing module 400 to perform the task or function. Additionally, the steps of the methods may be performed in any feasible chronological order, regardless of the order shown in the figures or the order in which the steps are described.

Figure 13:
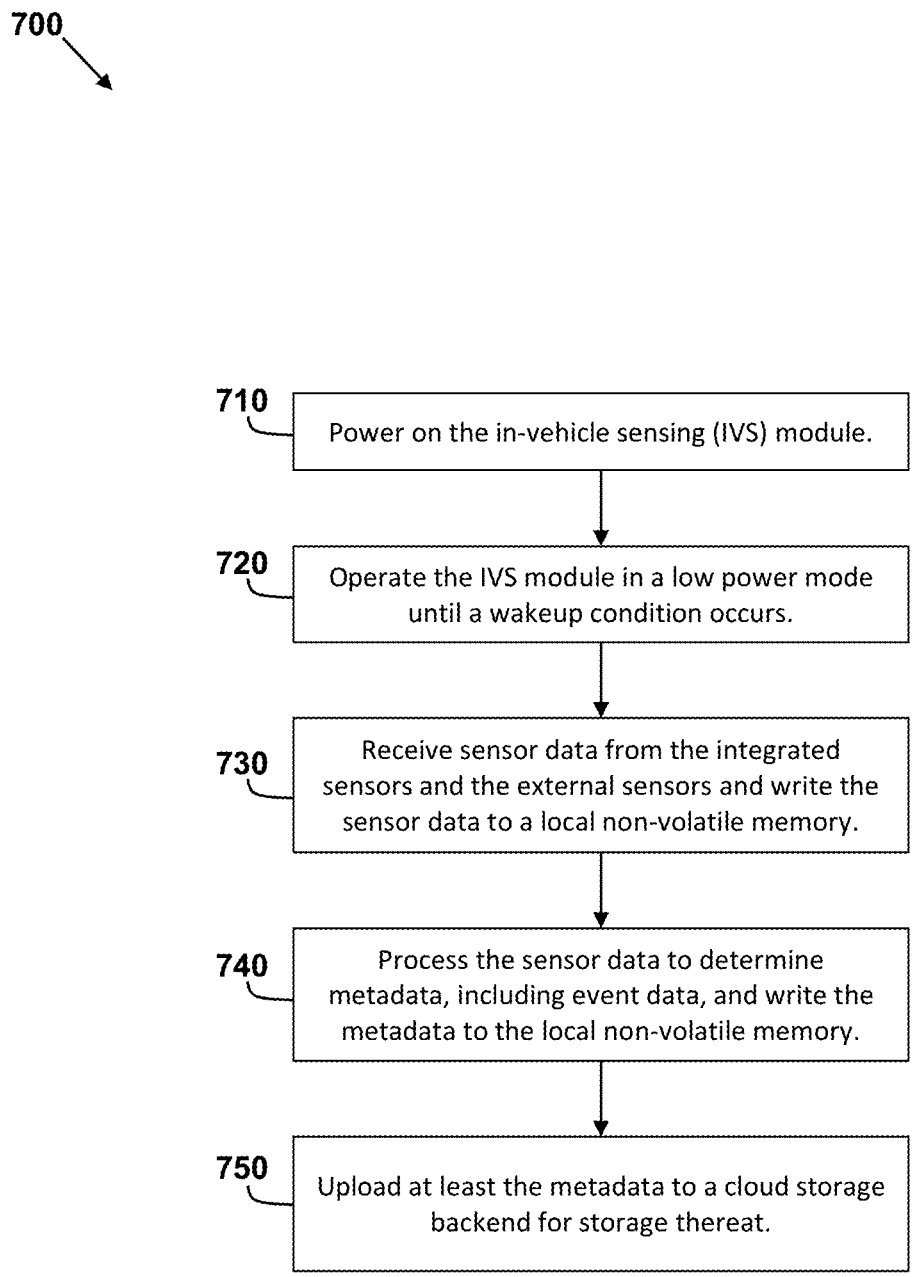
FIG. 13 is a process diagram illustrating a method of operating the in-vehicle sensing module of FIG. 7.

FIG. 13 shows a method 700 for operating the in-vehicle sensing module 400 to monitor at least the cabin 108 of a shared vehicle 102. The method 700 advantageously captures, and stores in a non-volatile memory (e.g. memory 484 and/or removable memory storage device 524), sensor data during operation of the shared vehicle 102, for example in the context of a shared vehicle service, such as car rental service, an autonomous taxi service, a ride sharing service, or the like. Moreover, the method 700 advantageously processes the sensor data to provide metadata, which is also stored in the non-volatile memory 484 and/or 524. The method 700 advantageously enables operators of such shared vehicle services to monitor the condition of the shared vehicle 102, enforce rules and policies, and provide additional benefits to the customer with minimal human intervention.

The method 700 begins with powering on the in-vehicle sensing module (block 710). Particularly, as noted above, the battery monitoring circuitry 560 is configured to monitor a voltage and current of the power line 140 provided via the external cable 544 to the external I/O connector 540. In some embodiments, the power line 140 is provided via an always-on power line of the shared vehicle 102, which directly provides the battery voltage of the vehicle battery 136. It will be appreciated that, if precisely measured, the battery voltage of the vehicle battery 136 can be used to estimate a state of charge of the vehicle battery 136. In one embodiment, the battery monitoring circuitry 560 measures the battery voltage provided via the external cable 544 and, in response to the battery voltage exceeding a predetermined threshold voltage, provides a turn-on signal to the controller 460 to at least partially turn on the in-vehicle sensing module 400. The predetermined threshold voltage is a battery voltage corresponding to a predetermined state of charge of the vehicle battery. In one embodiment, the predetermined state of charge is one at which the vehicle battery 136 can still provide sufficient amperage to start the vehicle. In this way, the in-vehicle sensing module 400 will only operate with battery power if the vehicle battery 136 is sufficiently charged and will not cause the vehicle battery to unnecessarily drain if the shared vehicle 102 is not started for an extended period of time.

In alternative embodiments, the power line 140 connected to via the I/O connector 540 is a switched/accessory power line of the shared vehicle 102, which only provides the battery voltage of the vehicle battery 136 if the ignition has been activated to start the shared vehicle 102 (generally by toggling an operating element of the ignition while pressing the brakes) or if accessory power of the shared vehicle 102 has been activated (generally by toggling an operating element of the ignition without pressing the brakes). Thus, in response to detecting the battery voltage from the vehicle battery 136, the battery monitoring circuitry 560 provides a turn-on signal to the controller 460 to at least partially turn on.

The method 700 continues with operating the in-vehicle sensing module in a low power mode until a wakeup condition occurs (block 720). Particularly, in response to the turn-on signal, the in-vehicle sensing module 400 begins operation in a low power mode in which the controller 460 activates a subset of components of the in-vehicle sensing module 400 to turn on. Particularly, in one exemplary embodiment, in the low-power mode, only the IMU 564, the environmental sensor 568, the ignition sensing circuitry 556, and the low power supply 552 of the power supply circuitry 548 are activated. Additionally, the controller 460 itself may operate in a low power state in which certain functionalities or sub-components, such as those related to cellular telephony and GNSS, are disabled.

The in-vehicle sensing module 400 operates in the low power mode until a wakeup condition is satisfied or, more particularly, until the controller 460 receives a wakeup signal. In response to receiving the wakeup signal, the in-vehicle sensing module 400 begins operation in an active mode in which the controller 460 activates all of the components of the in-vehicle sensing module 400 to turn on. In one embodiment, the ignition sensing circuitry 556 sends a wakeup signal to the controller 460 in response to detecting that the ignition of the shared vehicle 102 has been activated. In one embodiment, the IMU 564 sends a wakeup signal to the controller 460 in response to detecting a disturbance of the shared vehicle 102 (e.g., acceleration or gyroscopic measurements exceeding a threshold or matching a predetermined profile) indicating, for example, that a driver has unlocked the shared vehicle 102 and entered the cabin 108. In one embodiment, if the cellular telephony functionality of the controller 460 is operational during low-power mode, the wakeup signal can be received from the cloud storage backend 150.

The method 700 continues with receiving sensor data from the integrated sensors and the external sensors and writing the sensor data to a local non-volatile memory (block 730). Particularly, in the active mode, after receiving the wakeup signal, the controller 460 begins recording/writing sensor data from the integrated sensors and from the external sensors to the removable memory storage device 524, the memory 484, or to some other non-volatile memory. In one embodiment, the IoT controller 460 implements one or more ring buffers (which may also be referred to as circular buffers, circular queues, or a cyclic buffers) on the removable memory storage device 524 to manage storage of newly measured sensor data and the deletion of old sensor data.

The method 700 continues with processing the sensor data to determine metadata, including event data, and writing the metadata to the local non-volatile memory (block 740). Particularly, the controller 460 is configured to process the sensor data received from the integrated sensors or from the external sensors to enrich the data with metadata and, in particular, event detection. As discussed above, the sensors may comprise a wide variety of sensors including cameras (e.g. external camera 612), microphones (e.g. microphones 580), gyroscopes and accelerometers (e.g. IMU 564), smoke detectors (e.g. particle sensor 412) or other air-quality/particle sensors (e.g. environmental sensor 568), temperature sensors, and/or humidity sensors. The controller 460 processes the sensor data to determine one or more conditions, qualities, or statuses of the shared vehicle 102 and/or detect the occurrence of one or more events related to the one or more conditions, qualities, or statuses of the shared vehicle 102. The IoT controller 460 stores the determined conditions, qualities, or statuses and the detected events related thereto on the memory 484 and/or the removable memory storage device 524 as metadata of the stored sensor data.

In at least some embodiments, the controller 460 is configured to determine one or more conditions, qualities, or statuses of the shared vehicle 102 and/or detect the occurrence of one or more events related to the one or more conditions, qualities, or statuses of the shared vehicle 102, using an algorithm or model, such as a machine learning model (e.g., an artificial neural network). In one embodiment, the controller 460 is configured to receive updates for the algorithm or model from the cloud storage backend 150, via the cellular telephony modem thereof.

In some embodiment, in response to detecting a particular quality, condition, status, or event, the controller 460 operates the camera trigger circuitry 608 to cause the vehicle camera 612 to capture an image or video of the cabin 108. The controller 460 stores the captured image on the memory 484 and/or the removable memory storage device 524 as metadata of the sensor data from which the particular quality, condition, status, or event was detected.

In some embodiments, the controller 460 is configured to determine whether the shared vehicle 102 has been involved in a collision or has been otherwise mechanically damaged based on the acceleration and gyroscopic measurements provided by the IMU 564 or by a similar external sensor (e.g. sensor 120). In one embodiment, the controller 460 is configured to detect a collision or damage event in response to the acceleration and/or the gyroscopic measurements exceeding a predetermined threshold or matching with a predetermined acceleration profile. In one embodiment, the controller 460 executes a machine learning model (e.g., an artificial neural network) to detect a collision or damage event based on the acceleration and/or the gyroscopic measurements. In one embodiment, the controller 460 detects where the damage occurred (e.g., front left) and classifies a severity or grade of damage (e.g., hard), based on the acceleration and/or the gyroscopic measurements or other sensor data. In one embodiment, the controller 460 executes a machine learning model (e.g., an artificial neural network) to classify the detected a collision or damage based on the acceleration and/or the gyroscopic measurements. In one embodiment, in response to a collision or damage event, the controller 460 operates the camera trigger circuitry 608 to cause the vehicle camera 612 to capture an image or video of the cabin 108.

In some embodiments, the controller 460 is configured to determine whether the cabin 108 of the shared vehicle 102 has an unpleasant or abnormal odor based on the VOC measurements provided by the environmental sensor 568. In one embodiment, the controller 460 is configured to detect an unpleasant/abnormal odor event in response to the VOC measurements exceeding a predetermined threshold or matching with a predetermined profile. In one embodiment, the controller 460 executes a machine learning model (e.g., an artificial neural network) to detect an unpleasant/abnormal odor event based on the VOC measurements. In one embodiment, in response to an unpleasant/abnormal odor event, the controller 460 operates the camera trigger circuitry 608 to cause the vehicle camera 612 to capture an image or video of the cabin 108.

Additionally, the controller 460 may be configured in some embodiments to identify and/or categorize the scents or smells present in the cabin 108 of the shared vehicle 102 based at least on the VOC measurements provided by the environmental sensor 568. For instance, based on the chemical profile of the VOCs sensed in the cabin 108, and, in some embodiments, in conjunction with the sensed temperature, humidity, barometric pressure, and particulate concentrations, the controller 460 identifies the scent as corresponding to a particular category of odors. For example, in some embodiments, the controller 460 is configured to identify and categorize odors corresponding to one or more of: marijuana, tobacco, perfume, food, beverages, alcohol, urine, vomit, feces, animal odors, mold, gasoline, and other odors that may be detectable to users of the vehicle 102. In one embodiment, the controller 460 is configured to execute a machine learning model (e.g., an artificial neural network) to identify and categorize the odors in the vehicle cabin 108 based on the detected VOCs and, in some embodiments, further based on the temperature, humidity, pressure, and/or particle measurements. In some embodiments, in response to detection of certain categories of odors, the controller 460 operates the camera trigger circuitry 608 to cause the vehicle camera 612 to capture an image or video of the cabin 108.

In some embodiments, the controller 460 is configured to determine whether a driver or passenger is smoking within the cabin 108 of the shared vehicle 102 based on the particulate matter measurements provided by the particle sensor 564. In one embodiment, the controller 460 is configured to monitor a curve of the particulate matter concentrations over time and detect a smoking event in response to the curve of particulate matter concentrations matching the reference profile/curve or exceeding the threshold concentration. In one embodiment, the controller 460 executes a machine learning model (e.g., an artificial neural network) to detect a smoking event based on the particulate matter measurements. In one embodiment, in response to a smoking event, the controller 460 operates the camera trigger circuitry 608 to cause the vehicle camera 612 to capture an image or video of the cabin 108.

The method 700 continues with uploading at least the metadata to a cloud storage backend for remote storage (block 750). Particularly, the controller 460 is configured to operate the cellular telephony modem 488 to upload at least the determined metadata to the cloud storage backend 150. The uploaded metadata at least includes the detected events and may include corresponding timestamps indicating the time at which each event occurred, as well as other contextual information regarding the detected events (e.g., an image captured in response to detecting an event). In some embodiments, the controller 460 is configured to also upload the raw sensor data from which an event was detected, or intermediate data determined during the processing of the sensor data to detect an event. In some embodiments, the controller 460 is configured to upload all of the raw sensor data, regardless of whether the sensor data correspond to any detected events. In one embodiment, the in-vehicle sensing module 400 utilizes a secured and encrypted (TLS V1.2 encryption) connection to the cloud storage backend 150 using a public key infrastructure (PKI), or equivalent. In one embodiment, authentication is ensured by usage of certificates, which are signed by appropriate certificate authorities.

Additional Embodiments

The reader should appreciate that, in some embodiments, features disclosed above with regard to the in-vehicle sensing module 112 are integrated in the in-vehicle sensing module 400. For instance, in some embodiments, the in-vehicle sensing module 400 includes a camera, a heatsink, and/or a SoM configuration. Likewise, the in-vehicle sensing module 112 includes features described above with regard to the in-vehicle sensing module 400. For example, in some embodiments, the in-vehicle sensing module 112 includes an environmental sensor, or a SoC configured as described with reference to the in-vehicle sensing module 400.

Additionally, in various embodiments, any or all of the functions and operations described above for the in-vehicle sensing module 112 are integrated in the in-vehicle sensing module 400. For example, in one embodiment of the in-vehicle sensing module 400, the controller 460 is configured to analyze photos captured by an integrated camera or by the external camera 612 in a manner similar to that described above with reference to FIGS. 4-6. Likewise, embodiments of the in-vehicle sensing module 112 are configured to execute any one or more of the method steps of the method 700 described herein.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

The invention claimed is:

1. A sensing module for monitoring a cabin of a vehicle, comprising:
    an environmental sensor configured to sense organic compounds in ambient air of the cabin;
    a particle sensor configured to detect particulate matter in the ambient air of the cabin;
    a controller operably connected to the environmental sensor and the particle sensor and configured to receive sensor signals from the environmental sensor and the particle sensor and to transmit data to a remote server via the Internet;

a housing configured to mount to a windshield of said vehicle, the housing supporting the environmental sensor, the particle sensor, and the controller, wherein the housing defines a substantially enclosed interior space in which the environmental sensor, the particle sensor, and the controller are arranged; and a printed circuit board (PCB) supported in the housing and which operably connects the controller, the environmental sensor, and the particle sensor to one another, wherein the controller and the environmental sensor are arranged on the printed circuit board.

2. The sensing module of claim 1, wherein the housing includes a separator that at least substantially isolates a first interior region of the interior space from a second interior region of the interior space.

3. The sensing module of claim 2, wherein the particle sensor includes an inlet and an outlet, the inlet opening to the first interior region and the outlet opening into the second interior region.

4. The sensing module of claim 3, wherein a volume of the inlet first interior region is less than 10% of an overall volume of the interior space.

5. The sensing module of claim 4, wherein the housing defines at least one first opening that opens into the first interior region, and at least one second opening that opens into the second interior region.

6. The sensing module of claim 5, wherein the environmental sensor is arranged in the second interior region.

7. The sensing module of claim 1, further comprising:
at least one microphone supported in the housing and operably connected to the controller.

8. The sensing module of claim 7, wherein:
the housing includes at least one cylindrical projection and defines at least one third opening that opens into the at least one cylindrical projection; and
each microphone of the at least one microphone is arranged within an associated one of the at least one cylindrical projections.

9. The sensing module of claim 8, further comprising:
an acoustic gasket that seals against the PCB and circumferentially seals against each one of the at least one cylindrical projections so as to acoustically isolate the associated microphone inside the cylindrical projection.

10. The sensing module of claim 1, further comprising:
a cellular telephony modem arranged on the PCB, the controller configured to transmit the data to the remote server via the cellular telephony modem.

11. The sensing module of claim 10, wherein the controller is configured as a system on a chip ("SoC"), and the cellular telephone modem is integrated in the SoC.

12. The sensing module of claim 1, wherein the printed circuit board includes a connector configured to connect the printed circuit board to the particle sensor.

13. A sensing module for monitoring a cabin of a vehicle, comprising:

an environmental sensor configured to sense organic compounds in ambient air of the cabin;

a particle sensor configured to detect particulate matter in the ambient air, the particle sensor including an inlet;

a controller operably connected to the environmental sensor and the particle sensor and configured to receive sensor signals from the environmental sensor and the particle sensor and to transmit data to a remote server via the Internet; and a housing configured to mount to a windshield of said vehicle, the housing defining an interior space in which the environmental sensor, the particle sensor, and the controller are supported, the interior space having an inlet region from which the inlet of the particle sensor draws air, the inlet region being substantially isolated from a remainder of the interior space and having a volume that is less than 10% of an overall volume of the interior space.

14. The sensing module of claim 13, wherein the environmental sensor is further configured to sense temperature, barometric pressure, and relative humidity of the ambient air.

15. A sensing module for monitoring a cabin of a vehicle, comprising:

an environmental sensor configured to sense organic compounds in ambient air of the cabin;

a particle sensor configured to detect particulate matter in the ambient air;

a controller operably connected to the environmental sensor and the particle sensor and configured to receive sensor signals from the environmental sensor and the particle sensor and to transmit data to a remote server via the Internet;

a printed circuit board ("PCB") supported in the housing and which operably connects the controller, the environmental sensor, and the particle sensor to one another, the controller and the environmental sensor arranged on the PCB;

at least one microphone arranged on the PCB; and a housing configured to mount to a windshield of said vehicle, the housing supporting the environmental sensor, the particle sensor, the controller, and the PCB, the housing including at least one opening assigned to each microphone of the at least one microphone.

16. The sensing module of claim 15, wherein the housing defines a substantially enclosed interior space in which the environmental sensor, the particle sensor, and the controller are arranged.

17. The sensing arrangement of claim 15, wherein the housing defines an interior space, and each microphone is arranged in a microphone space of the interior space that is acoustically isolated from a remainder of the interior space.

18. The sensing arrangement of claim 17, further comprising:
an acoustic gasket circumferentially surrounding each microphone of the at least one microphone so as to acoustically isolate the associated microphone space.

* * * * *